United States Patent
Peng et al.

(10) Patent No.: US 9,328,317 B2
(45) Date of Patent: *May 3, 2016

(54) FLUOROPHOSPHATE SURFACTANTS

(75) Inventors: Sheng Peng, Hockessin, DE (US);
Allison Mary Yake, Landenberg, PA (US); Xianjun Meng, Hockessin, DE (US)

(73) Assignee: THE CHEMOURS COMPANY FC, LLC, Wilmington, DE (US)

( * ) Notice: Subject to any disclaimer, the term of this patent is extended or adjusted under 35 U.S.C. 154(b) by 1110 days.

This patent is subject to a terminal disclaimer.

(21) Appl. No.: 13/400,176

(22) Filed: Feb. 20, 2012

(65) Prior Publication Data
US 2013/0112908 A1    May 9, 2013

Related U.S. Application Data

(60) Provisional application No. 61/556,418, filed on Nov. 7, 2011.

(51) Int. Cl.
*C09K 3/18* (2006.01)
*C11D 1/00* (2006.01)
*C07F 9/6574* (2006.01)
*C07F 9/09* (2006.01)

(52) U.S. Cl.
CPC ............ *C11D 1/006* (2013.01); *C07F 9/091* (2013.01); *C07F 9/65742* (2013.01)

(58) Field of Classification Search
CPC .......... C11D 1/006; C11D 1/00; C11D 1/345; C11D 1/347; C11D 17/00; C07F 9/65742; C07F 9/091; C07F 9/09; C07F 9/141; C07F 9/6574; C07F 9/201; C07F 9/16; C07F 9/1651; C07F 9/1411; A62D 1/00; A62D 1/0085; C07C 229/02; C08K 5/521; C08K 5/527; C08K 5/5398; C08L 71/02; C09D 7/06; C09D 5/02; C09D 7/12; C09D 11/00; C09D 121/02; C09D 167/06; C09D 167/08; C09D 175/04; C09K 3/00; C09K 3/18; C09K 8/035; C09K 8/584; C09K 13/00; C09K 13/08; C09G 1/00
USPC .............. 516/199; 558/70, 71, 168, 169, 188, 558/183, 186, 195, 196; 987/202, 203, 204, 987/209, 224
See application file for complete search history.

(56) References Cited

U.S. PATENT DOCUMENTS

| | | | |
|---|---|---|---|
| 3,083,224 A | 3/1963 | Brace | |
| 3,952,075 A * | 4/1976 | Nakamura et al. | 558/186 |
| 3,979,469 A | 9/1976 | Jager | |
| 4,064,067 A | 12/1977 | Lore | |
| 4,145,382 A | 3/1979 | Hayashi et al. | |
| 4,497,720 A | 2/1985 | Moriga et al. | |
| 4,751,320 A * | 6/1988 | Masuda et al. | 558/92 |
| 4,898,700 A * | 2/1990 | Yoshinari | D01F 9/22 264/130 |
| 5,021,319 A * | 6/1991 | Kakimi | G03F 7/0285 430/138 |
| 5,091,550 A * | 2/1992 | Falk et al. | 558/165 |
| 5,266,724 A * | 11/1993 | Kai et al. | 562/567 |
| 5,481,028 A | 1/1996 | Petrov et al. | |
| 5,491,261 A * | 2/1996 | Haniff et al. | 562/582 |
| 6,271,289 B1 | 8/2001 | Longoria et al. | |
| 6,315,822 B1 * | 11/2001 | Oharu et al. | 106/2 |
| 6,447,588 B1 * | 9/2002 | Funaki et al. | 106/2 |
| 7,645,731 B1 | 1/2010 | Silvernail et al. | |
| 8,859,799 B1 * | 10/2014 | Larichev et al. | 558/175 |
| 2003/0008251 A1 * | 1/2003 | Yamaguchi | G03C 1/49863 430/598 |
| 2009/0181190 A1 * | 7/2009 | Tsubaki | B41M 7/0027 428/32.77 |
| 2011/0091408 A1 * | 4/2011 | Raghavanpillai | 424/78.08 |
| 2011/0092410 A1 | 4/2011 | Raghavanpillai | |

FOREIGN PATENT DOCUMENTS

| | | |
|---|---|---|
| EP | 0312962 A2 | 4/1989 |
| EP | 0102240 B1 | 10/1990 |
| EP | 0690039 B1 | 8/2006 |
| JP | 2002196459 A | 7/2002 |
| JP | 2007154101 A | 6/2007 |
| WO | 9511877 A1 | 5/1995 |

OTHER PUBLICATIONS

Machine Translation on Publ. No. JP2007154101 (A), published Jun. 2007, World Intellectual Property Organization Patentscope, Geneva, Switzerland, obtained online @ http://patentscope.wipo.int/search/en/search.jsf (Downloaded Apr. 5, 2015), pp. 1-9.*
Balague et al., Synthesis of fluorinated telomers, Part 1, Telomerization of vinylidene fluoride with perfluoroalkul iodides, Journal of Fluorine Chemistry, 1995, 70(2), 215-223, Elsevier.
Naud et al., Synthesis of terminally perfluorinated long-chain alkanethiols, sulfides and disulfides from the corresponding halides, Journal of Fluorine Chemistry, 2000, 104(2), 173-183, Elsevier.
International Preliminary Report on Patentability, PCT/US2012/036916, (mailed Aug. 16, 2012).

* cited by examiner

*Primary Examiner* — Daniel S Metzmaier

(57) ABSTRACT

This invention is directed to a composition capable of imparting surface effects to a liquid by contacting the liquid with a partially fluorinated phosphate with an ammonium cation $(NH_2R^1R^2)^+$ wherein $R^1$ and $R^2$ are independently linear or branched organic groups containing at least one carboxylate moiety and one amino moiety, and optionally be substituted, interrupted, or both with oxygen, sulfur, or nitrogen-containing moieties, or with cyclic alkyl or aryl moieties containing up to 10 carbon atoms.

15 Claims, No Drawings

FLUOROPHOSPHATE SURFACTANTS

FIELD OF INVENTION

The field of invention is related to fluorophosphates and their use as surfactants, additives for coatings or treating agents to impart water, oil, and oil repellency to substrates coated with such compositions.

BACKGROUND OF INVENTION

Commonly fluoroalkyl phosphate surfactants and surface treatment agents contain multiple fluorochemical chains, containing a higher percentage of fluorine at a given concentration and are typically used because they are thought to provide better performance. However, the fluorinated starting materials are more expensive and in short supply. Reduction of the amount of the fluorinated starting material in these surfactants while maintaining the same or better performance is desirable. Reducing the amount of the fluorinated starting component needed would not only reduce the cost, but also shorten the cycle time as fewer steps are needed in the production of the surfactants and less energy is required. Reducing the fluorine content would reduce the cost, but it is necessary to maintain product performance.

Brace and Mackenzie, in U.S. Pat. No. 3,083,224, describe mixed fluoroalkyl phosphates having the formula $[C_m F_{2m+1}C_nH_{2n}O]_y PO(OM)_{3-y}$, where m is 4 to 12, n is 1 to 16, and y is averaged to be 1.0 to 2.5. Brace and Mackenze describe their use as an oil repellent, particularly when y is 2.

Phosphate surfactants having ammonium as a counter ion can potentially release ammonia into the environment. Alternate counter ions need to be able to provide a stable surfactant, while also providing no adverse effects to the surfactant performance.

It is desirable to improve surfactant performance, in particular lowering of surface tension in coating compositions while using less fluorinated starting materials and a counter ion other than simple ammonium compounds. It is also desirable to impart improved surface effects to coated surfaces. The present invention provides a method to increase surfactant performance and to impart improved surface effects to a coated surface while utilizing less fluorinated starting material.

SUMMARY OF THE INVENTION

The present invention comprises a composition comprising formula I, formula II, or formula III

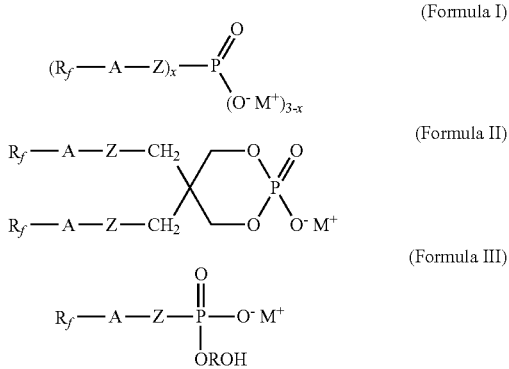

wherein $R_f$ is a $C_1$ to $C_6$ linear or branched perfluoroalkyl optionally interrupted by one, two or three ether oxygen atoms;

x is 1 to 2;

A is $(CH_2)_k$, $(CH_2CF_2)_m(CH_2)_n$, $(CH_2)_o SO_2 N(CH_3)(CH_2)_p$, $O(CF_2)_2(CH_2)_r$, or $OCHFCF_2 OE$;

Z is O or S;

m is 1 to 4;

k, n, o, p, and r are each independently 1 to 20;

E is a $C_2$ to $C_{20}$ linear or branched alkyl group optionally interrupted by oxygen, sulfur, or nitrogen atoms; a cyclic alkyl group, or a $C_6$ to $C_{10}$ aryl group;

R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2; and M is an ammonium cation $(NH_2R^1R^2)^+$ wherein $R^1$ and $R^2$ are independently linear or branched organic groups containing at least one carboxylate moiety and one amino moiety, and optionally be substituted, interrupted, or both with oxygen, sulfur, or nitrogen-containing moieties, or with cyclic alkyl or aryl moieties containing up to 10 carbon atoms.

Another aspect of the invention is a method of providing lowering surface tension, water repellency, oil repellency and stain resistance to a substrate comprising contacting the substrate with a composition comprising one or more compounds of formula (I), (II) or (III).

Another aspect of the invention is a method of providing resistance to blocking, open time extension and oil repellency to a substrate having deposited thereon a coating composition comprising adding to the coating composition, prior to deposition on the substrate, a composition comprising one or more compounds of formula (I), (II) or (III).

Another embodiment of the invention is a substrate to which has been applied a composition of comprising one or more compounds of formula (I), (II) or (III).

DETAILED DESCRIPTION OF INVENTION

Hereinafter trademarks are designated by upper case.

The present invention comprises a composition comprising formula I, formula II, or formula III

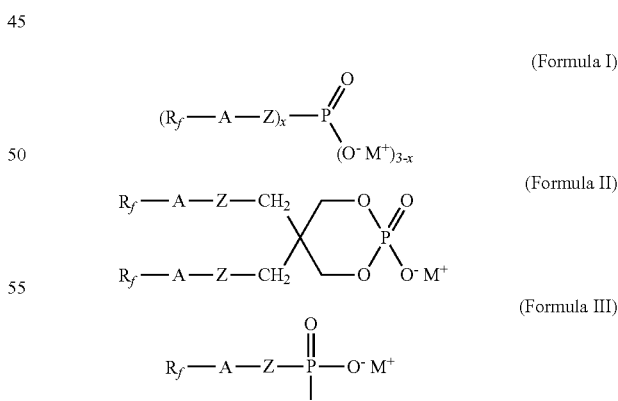

wherein $R_f$ is a $C_1$ to $C_6$ linear or branched perfluoroalkyl optionally interrupted by one, two or three ether oxygen atoms;

x is 1 to 2;

A is $(CH_2)_k$, $(CH_2CF_2)_m(CH_2)_n$, $(CH_2)_o SO_2 N(CH_3)(CH_2)_p$, $O(CF_2)_2(CH_2)_r$, or $OCHFCF_2 OE$;

Z is O or S;

m is 1 to 4;

k, n, o, p, and r are each independently 1 to 20;

E is a $C_2$ to $C_{20}$ linear or branched alkyl group optionally interrupted by oxygen, sulfur, or nitrogen atoms; a cyclic alkyl group, or a $C_6$ to $C_{10}$ aryl group;

R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2; and M is an ammonium cation $(NH_2R^1R^2)^+$ wherein $R^1$ and $R^2$ are independently linear or branched organic groups containing at least one carboxylate moiety and one amino moiety, and optionally be substituted, interrupted, or both with oxygen, sulfur, or nitrogen-containing moieties, or with cyclic alkyl or aryl moieties containing up to 10 carbon atoms.

Fluorinated compounds of formula (I), (II), and (III) described above useful in various embodiments of the invention are available by synthesis.

The fluoroalkylphosphates of formula (I) and (II) are prepared according to the method described by Longoria et al in U.S. Pat. No. 6,271,289, and Brace and Mackenzie, in U.S. Pat. No. 3,083,224, each herein incorporated by reference. Typically, either phosphorus pentoxide ($P_2O_5$) or phosphorus oxychloride ($POCl_3$) is reacted with the fluoroalkyl alcohol or fluoroalkyl thiol to give mixtures of the mono- and bis(fluoroalkyl)phosphoric acids. Neutralization with an amino acid, such as L-arginine and L-lysine, for instance, provides the corresponding phosphates. Reacting an excess of fluoroalkyl alcohol or fluoroalkyl thiol with $P_2O_5$ followed by neutralization provides a mixture of mono(fluoroalkyl)phosphate and bis(fluoroalkyl)phosphate. Higher ratios of bis(fluoroalkyl)phosphate to mono(fluoroalkyl)phosphate are obtained by using the method of Hayashi and Kawakami in U.S. Pat. No. 4,145,382. The phosphite and phosphinate compositions are prepared in a similar manner.

The resulting composition is then diluted with water, mixture of water and solvent, or further dispersed or dissolved in a solvent selected from the groups comprising simple alcohols, glycol ethers, and ketones that are suitable as the solvent for final application to substrates (hereinafter the "application solvent"). Alternatively, an aqueous dispersion, made by conventional methods with surfactants, is prepared by removing solvents by evaporation and the use of emulsification or homogenization procedures known to those skilled in the art. Such solvent-free emulsions may be preferred to minimize flammability and volatile organic compounds (VOC) concerns. The final product for application to a substrate can be a dispersion, if water based, or a solution.

The fluoroalkylphosphates of formula (III) are prepared by reacting either phosphorus pentoxide ($P_2O_5$) or phosphorus oxychloride ($POCl_3$) with fluorinated alcohol, followed by the addition of hydrocarbon diol or poly(glycol). Typically the phosphorus pentoxide or phosphorus oxychloride is added to the fluorinated alcohol in an amount that is approximately equivalent mol percent. For example, when phosphorus pentoxide is used from about 0.4 to about 1.6 mole equivalent of fluorinated alcohol to $P_2O_5$ is added. The mixture is heated to a temperature of from about 70° C. to about 120° C., preferably to from about 100° C. to about 110° C., and maintained for several hours, preferably from about 3 to about 15 hours. A diol or poly(glycol) is then added to the reaction mixture with continued heating at the above temperature for an additional time of from about 3 to about 15 hours. The mole ratio of diol or poly(glycol) to $P_2O_5$ is from about 1.4 to about 2.6. This is followed by the optional addition of a surfactant in from about 1% to about 3% by weight. Any of a variety of surfactants can be employed, such as TERGITOL available from Sigma Aldrich, St. Louis, Mo. After about 1 to about 2 hours, ammonia is added with mixing, followed by water, to provide the phosphate of Formula 1.

Diols useful in the synthesis of compounds of Formula (III) include $C_2$ to $C_{60}$ straight and branched chain alcohols optionally having one or two double bonds. Examples include 1,3-propanediol; propylene glycol (1,2-propanediol); di(ethylene glycol); tri(ethylene glycol); tetra(ethylene glycol); poly(ethylene glycol)s [$PEG(OH)_2$], preferably having from about 4 to about 20 repeat units, and more preferably from about 5 to about 15 repeat units; poly(ethylene glycol)-polypropylene glycol-poly(ethylene glycol) triblock polymers [PEG-PPG-PEG-$(OH)_2$]; and random copolymers of ethylene oxide and propylene oxide, preferably with a molecular weight $M_w$ of from about 200 to about 1250. Poly(1,3-propanediol)s are available from E. I. du Pont de Nemours and Company, Wilmington, Del. Polyethylene glycols with nominal molecular weights of 200 to 2000 are available from Aldrich Chemical Company, St. Louis, Mo. Tri-block copolymers of polyethylene oxide and polypropylene oxide (PEG-PPG-PEG) are available from BASF, Mount Olive, N.J.

It will be apparent to one skilled in the art that many changes to any or all of the procedures described above may also be used to optimize the reaction conditions for obtaining maximum yield, productivity or product quality.

The fluoroalkyl alcohol used as a reactant in the preparation of composition comprising formula (I), (II), or (III) are described below for various embodiments.

One embodiment of the present invention is a composition comprising formula (I), (II), or (III), where A is $(CH_2)_k$. Fluorinated alkyl iodides of formula $R_f$—I can be treated with ethylene by procedures described in U.S. Pat. No. 3,979,469, (Ciba-Geigy, 1976) to provide the telomer ethylene iodides wherein k is 2 to 6, or higher. The telomer ethylene iodides can be treated with oleum and hydrolyzed to provide the corresponding telomer alcohols according to procedures disclosed in WO 95/11877 (Elf Atochem S.A.). Fluorinated alcohols $C_6F_{13}CH_2CH_2OH$ and $C_4F_9CH_2CH_2OH$ are available from E. I. du Pont de Nemours and Company, Wilmington, Del. The higher homologs of telomer ethylene iodides are available with excess ethylene at high pressure. The telomer ethylene iodides can be treated with a variety of reagents to provide the corresponding thiols according to procedures described in J. Fluorine Chemistry, 104, 2 173-183 (2000). One example is the reaction of the telomer ethylene iodides with sodium thioacetate, followed by hydrolysis.

One embodiment of the present invention is a composition comprising formula (I), (II), or (III), wherein A is $(CH_2CF_2)_m(CH_2)_n$.

The telomerization of vinylidene fluoride (VDF) with linear or branched perfluoroalkyl iodides is well known, and produces compounds of the structure $R_f(CH_2CF_2)_mI$, wherein, m is 1 to 3 or more and $R_f$ is a $C_1$ to $C_6$ linear or branched perfluoroalkyl group. For example, see Balague, et al, "Synthesis of fluorinated telomers, Part 1, Telomerization of vinylidene fluoride with perfluoroalkyl iodides", J. Flour Chem. (1995), 70(2), 215-23. The specific telomer iodides of formula $R_f(CH_2CF_2)_pI$ are isolated by fractional distillation and can be treated with ethylene, as described above, to produce compounds of formula $R_f(CH_2CF_2)_m(CH_2)_nI$. The compounds of formula $R_f(CH_2CF_2)_m(CH_2)_nI$ can be treated as described above to produce alcohols and thiols.

One embodiment of the present invention is a compound composition comprising formula (I), (II), or (III), A is $(CH_2)_o SO_2N(CH_3)(CH_2)_p$—. Preferred compositions of formula (I), (II), or (II), include those wherein o and p are each 2. The fluoroalkyl alcohol used to prepare compounds of $R_f(CH_2)_o SO_2N(CH_3)(CH_2)_p$—OH is available from E. I. du Pont de Nemours and Company, Wilmington Del. Alternatively the fluoroalkyl alcohol $R_f(CH_2)_o SO_2N(CH_3)(CH_2)_p$—OH, wherein o and p are defined above in Formula (I), is prepared by the reaction of a fluoroalkyl ethylene iodide with potassium thiocyanate in water. The product $R_f(CH_2)_o SCN$ is distilled as a colorless liquid, which then is converted to fluorinated sulfonyl chloride having the formula $R_f(CH_2)_o SO_2Cl$ by a reaction with chlorine and acetic acid over several hours at about 45-50° C. in an autoclave. The sulfonyl chloride is then reacted with an amine, for example, such as N-methylethanolamine, to produce the fluorinated alcohol of the formula $R_f(CH_2)_o SO_2N(CH_3)(CH_2)_p$—OH.

One embodiment of the present invention is a composition comprising formula (I), (II), or (III), A is $O(CF_2)_q(CH_2)_r$. Preferred compositions of formula (I) or (II) are those wherein $R_f$ is $O(CF_2)_q(CH_2)_r$, q and r are each 2, $R_f$ is $C_3F_7$. Preferred compositions of formula (III) are those wherein A is $O(CF_2)_q(CH_2)_r$, q and r are each 2, and $R_f$ is $C_3F_7R$ is $CH_2CH_2$.

The fluoroalcohols used as starting materials to make the compositions of compositions wherein A is $O(CF_2)_q(CH_2)_r$ are available by synthesis.

The starting perfluoroalkyl ether iodides of formula $R_fOCF_2CF_2I$ can be made by the procedure described in U.S. Pat. No. 5,481,028, in Example 8, which discloses the preparation of perfluoroalkyl ether iodides from perfluoro-n-propyl vinyl ether. Perfluoroalkyl ether iodide is then reacted with an excess of ethylene at an elevated temperature and pressure. While the addition of ethylene can be carried out thermally, the use of a suitable initiator is preferred. Preferably the initiator is a peroxide such as benzoyl peroxide, isobutyryl peroxide, propionyl peroxide, or acetyl peroxide. More preferably the peroxide is benzoyl peroxide. The temperature of the reaction is not limited, but a temperature in the range of 110° C. to 130° C. is preferred. The reaction time can vary with the initiator and reaction conditions, but 24 hours is usually adequate. The product is purified by any means that separates unreacted starting material from the final product, but distillation is preferred. Satisfactory yields up to 80% of theory have been obtained using about 2.7 mols of ethylene per mole of perfluoalkyl ether iodide, a temperature of 110° C. and autogenous pressure, a reaction time of 24 hours, and purifying the product by distillation.

The perfluoroalkylether ethylene iodides of formula $R_fO(CF_2)_2(CH_2)_rI$, where $R_f$ and r are as defined above, are treated with oleum and hydrolyzed to provide the corresponding alcohols according to procedures disclosed in WO 95/11877 (Elf Atochem S.A.). Alternatively, the perfluoroalkylether ethyl iodides can be treated with N-methyl formamide followed by ethyl alcohol/acid hydrolysis. A temperature of about 130° to 160° C. is preferred. The higher homologs (r is >2) are available with excess ethylene at high pressure. The fluorinated alkyl ether ethylene iodides of formula $R_fO(CF_2)_2(CH_2)_rI$ are treated with a variety of reagents to provide the corresponding thiols according to procedures described in J. Fluorine Chemistry, 104, 2 173-183 (2000). The fluorinated alkyl ether ethylene iodides can also be treated to provide the corresponding thioethanols or thioethylamines by conventional methods.

One embodiment of the present invention is a composition comprising formula (I), (II), or (III), A is $OCHFCF_2OE$. The fluoroalcohols used as starting materials to make the compositions of Formula 5 are prepared by reacting a dioxane with a diol in the presence of an alkali metal compound. For example a dioxane and a perfluoroalkyl ether of formula $R_fOCF=CF_2$ are reacted with a diol such as $HO(CH_2)_2OH$ in the presence of an alkali metal, such as KOH, typically in a sealed stainless steel reaction vessel at about 70° C. for about 8 hours. The diol is used at about 1 to about 15 mols per mol of ether, preferably from about 1 to about 5 mols per mol of ether. Suitable alkali metal compounds include an alkali metal, alkali earth metal, alkali hydroxide, alkali hydride, or an alkali amide. Preferred are alkali metals such as Na, K or Cs, or alkali hydrides such as NaH or KH. The reaction is conducted at a temperature of from about 40° C. to about 120° C. The reaction can be conducted in an optional solvent, such as ether or nitrile.

The present invention comprises fluorinated aqueous mixtures comprising a mixture of an anionic aqueous fluoroalkyl phosphate, phosphite or phosphonite acid solution neutralized with an amino acid, preferably L-arginine and L-lysine. The composition is neutralized to a pH of about 5 to about 10, preferably about 6 to about 9 and most preferably, from about 6 to about 8.

One embodiment of the present invention is a method of lowering the surface tension of a liquid comprising contacting a liquid to a composition comprising formula I, formula II, or formula III

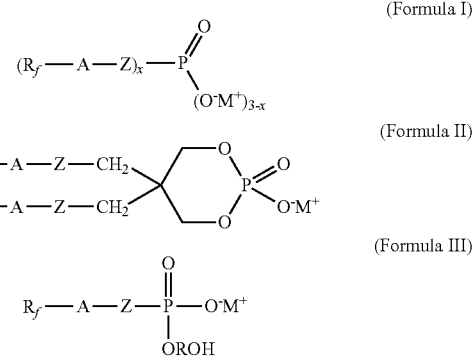

wherein $R_f$, x, A, Z, M, k, n, o, p, r, E, R, and M are as defined above.

The liquids where the present invention is useful to lower the surface tension include, but not limited to, are water, saline solution, KCl solution, drill fluids, well fluids, liquid treatment or gas treatment stream for subterranean formation and well bore areas, hydrocarbon, halocarbon system, coating composition, latex, polymer, floor finish, floor polish, fire fighting agent, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, or bonding agent.

Coating compositions are alkyd coatings, a Type I urethane coatings, an unsaturated polyester coatings, or a water-dispersed coatings.

The present invention further comprises a method of providing water repellency, oil repellency, and stain resistance to a substrate comprising contacting the substrate with a composition of formula (I) or (II) as defined above, or a mixture thereof. The composition of the present invention is typically applied by contacting the substrate with the composition by conventional means, including, but not limited to, brush, spray, roller, doctor blade, wipe, immersion, dip techniques, foam, liquid injection, and casting. Optionally, more than one coat can be used, particularly on porous surfaces.

The compositions of the present invention can be used as an additive during the manufacture of substrates. They can be added at any suitable point during manufacture. For example, in the case of paper, they can be added to the paper pulp in a size press. Preferably, about 0.3 weight % to about 0.5 weight % of the composition of the invention is added to paper pulp, based on the dry solids of the composition and dry paper fiber.

When used as a surface treatment for paper, the compositions of the invention are typically diluted with water to give an application solution having about 0.01 weight % to about 20 weight %, preferably about 0.1 weight % to about 10 weight %, and most preferably about 0.5 weight % to about 5 weight %, of the composition based on solids. The coverage as applied to paper is about 10 $g/m^2$ to about 200 $g/m^2$, and preferably about 10 $g/m^2$ to about 100 $g/m^2$ of the application solution. Preferably the application results in about 0.1 $g/m^2$ to about 5.0 $g/m^2$ of solids being applied to the paper.

When used on stone, tile and other hard surfaces, the compositions of the invention are typically diluted with water to give an application solution having about 0.1 weight % to about 20 weight %, preferably from about 1.0 weight % to about 10 weight %, and most preferably from about 2.0 weight % to about 5.0 weight %, of the composition based on solids. The coverage as applied to a substrate is about 100 g of application solution per sq meter ($g/m^2$) for semi-porous substrates (e.g. limestone) and 200 $g/m^2$ for porous substrates (e.g. Saltillo). Preferably the application results in about 0.1 $g/m^2$ to about 2.0 $g/m^2$ of solids being applied to the surface.

The composition of this invention is applied to or contacted with the substrate as such, or in combination with one or more other finishes or surface treating agents. The composition of the present invention optionally further comprises additional components such as treating agents or finishes to achieve additional surface effects, or additives commonly used with such agents or finishes. Such additional components comprise compounds or compositions that provide surface effects such as stain repellency, stain release, soil repellency, soil release, water repellency, oil repellency, antimicrobial protection, and similar effects. One or more of such treating agents or finishes can be blended with the composition of the present invention and applied to the substrate.

Other additives commonly used with such treating agents or finishes can also be present such as surfactants, pH adjusters, leveling agents, wetting agents, and other additives known by those skilled in the art. Examples of such finishes or agents include processing aids, foaming agents, lubricants, anti-stains, and the like. The composition is applied at a manufacturing facility, retailer location, or prior to installation and use, or at a consumer location.

The present invention further comprises a method of providing resistance to blocking, open time extension, and oil repellency to a substrate having deposited thereon a coating composition comprising adding to the coating composition prior to deposition on the substrate a composition of the above formula (I) or (II) or mixtures thereof. Suitable coating compositions, referred to herein by the term "coating base", include a composition, typically a liquid formulation, of an alkyd coating, Type I urethane coating, unsaturated polyester coating, or water-dispersed coating, and is applied to a substrate for the purpose of creating a lasting film on the substrate surface. These are conventional paints, stains, and similar coating compositions.

By the term "alkyd coating" as used herein is meant a conventional liquid coating based on alkyd resins, typically a paint, clear coating, or stain. The alkyd resins are complex branched and cross-linked polyesters containing unsaturated aliphatic acid residues. Conventional alkyd coatings utilize, as the binder or film-forming component, a curing or drying alkyd resin. Alkyd resin coatings contain unsaturated aliphatic acid residues derived from drying oils. These resins spontaneously polymerize in the presence of oxygen or air to yield a solid protective film. The polymerization is termed "drying" or "curing" and occurs as a result of autoxidation of the unsaturated carbon-carbon bonds in the aliphatic acid component of the oil by atmospheric oxygen. When applied to a surface as a thin liquid layer of formulated alkyd coating, the cured films that form are relatively hard, non-melting, and substantially insoluble in many organic solvents that act as solvents or thinners for the unoxidized alkyd resin or drying oil. Such drying oils have been used as raw materials for oil-based coatings and are described in the literature.

By the term "urethane coating" as used hereinafter is meant a conventional liquid coating based on Type I urethane resins, typically a paint, clear coating, or stain. Urethane coatings typically contain the reaction product of a polyisocyanate, usually toluene diisocyanate, and a polyhydric alcohol ester of drying oil acids. Urethane coatings are classified by ASTM D-1 into five categories. Type I urethane coatings contain a pre-reacted autoxidizable binder as described in Surface Coatings Vol. 1, previously cited. These are also known as uralkyds, urethane-modified alkyds, oil-modified urethanes, urethane oils, or urethane alkyds, are the largest volume category of polyurethane coatings and include paints, clear coatings, or stains. The cured coating is formed by air oxidation and polymerization of the unsaturated drying oil residue in the binder.

By the term "unsaturated polyester coating" as used hereinafter is meant a conventional liquid coating based on unsaturated polyester resins, dissolved in monomers and containing initiators and catalysts as needed, typically as a paint, clear coating, or gel coat formulation. Unsaturated polyester resins contain as the unsaturated prepolymer the product obtained from the condensation polymerization of a glycol such as 1,2-propylene glycol or 1,3-butylene glycol with an unsaturated acid such as maleic (or of maleic and a saturated acid, e.g., phthalic) in the anhydride form. The unsaturated prepolymer is a linear polymer containing unsaturation in the chain. This is dissolved in a suitable monomer, for instance styrene, to produce the final resin. The film is produced by copolymerization of the linear polymer and monomer by means of a free radical mechanism. The free radicals can be generated by heat, or more usually by addition of a peroxide, such as benzoyl peroxide, separately packaged and added before use. Such coating compositions are frequently termed "gel coat" finishes. In order that curing can take place at room temperature, the decomposition of peroxides into free radicals is catalyzed by certain metal ions, usually cobalt. The solutions of peroxide and cobalt compound are added separately to the mix and well stirred before application. The unsaturated polyester resins that cure by a free radical mechanism are also suited to irradiation curing using, for instance, ultraviolet light. This form of cure, in which no heat is produced, is particularly suited to films on wood or board. Other radiation sources, for instance electron-beam curing, are also used.

By the term "water-dispersed coatings" as used herein is meant coatings intended for the decoration or protection of a substrate composed of water as an essential dispersing component such as an emulsion, latex, or suspension of a film-forming material dispersed in an aqueous phase. "Water-dispersed coating" is a general classification that describes a number of formulations and includes members of the above described classifications as well as members of other classifications. Water-dispersed coatings general contain other common coating ingredients. Water-dispersed coatings are exemplified by, but not limited to, pigmented coatings such as latex paints, unpigmented coatings such as wood sealers, stains, and finishes, coatings for masonry and cement, and water-based asphalt emulsions. A water dispersed coating optionally contains surfactants, protective colloids and thickeners, pigments and extender pigments, preservatives, fungicides, freeze-thaw stabilizers, antifoam agents, agents to control pH, coalescing aids, and other ingredients. For latex paints the film forming material is a latex polymer of acrylate acrylic, vinyl-acrylic, vinyl, or a mixture thereof. Such water-dispersed coating compositions are described by C. R. Martens in "Emulsion and Water-Soluble Paints and Coatings" (Reinhold Publishing Corporation, New York, N.Y., 1965).

By the term "dried coating" as used herein is meant the final decorative and/or protective film obtained after the coating composition has dried, set or cured. Such a final film can be achieved by, for non-limiting example, curing, coalescing, polymerizing, interpenetrating, radiation curing, UV curing or evaporation. Final films can also be applied in a dry and final state as in dry coating.

Blocking is the undesirable sticking together of two coated surfaces when pressed together, or placed in contact with each other for an extended period of time. When blocking occurs separation of the surfaces can result in disruption of the coating on one or both surfaces. Thus improved resistance to blocking is beneficial in many situations where two coated surfaces need to be in contact, for example on window frames.

The term "open time extension" is used herein to mean the time during which a layer of liquid coating composition can be blended into an adjacent layer of liquid coating composition without showing a lap mark, brush mark, or other application mark. It is also called wet-edge time. Latex paint containing low boiling, volatile organic chemicals (VOC) has shorter than desired open-time due to lack of high boiling temperature VOC solvents. Lack of open time extension will cause surface defects such as overlapping brush marks or other marks. A longer open time extension is beneficial when the appearance of the coated surface is important, as it permits application of the coating without leaving overlap marks, brush marks, or other application marks at the area of overlap between one layer of the coating and an adjacent layer of the coating.

When used as additives the compositions of the present invention are effectively introduced to the coating base or other composition by thoroughly stirring it in at room or ambient temperature. More elaborate mixing can be employed such as using a mechanical shaker or providing heat or other methods. Such methods are not necessary and do not substantially improve the final composition. When used as an additive to latex paints, the compositions of the invention generally are added at about 0.001 weight % to about 5 weight % by dry weight of the composition of the invention in the wet paint. Preferably about 0.01 weight % to about 1 weight %, and more preferably 0.1 weight % to about 0.5 weight % is used.

The present invention also comprises substrates treated with the composition of the present invention. Suitable substrates include fibrous and hard surface substrates. The fibrous substrates include wood, paper, and leather. The hard surface substrates include porous and non-porous mineral surfaces, such as glass, stone, masonry, concrete, unglazed tile, brick, porous clay and various other substrates with surface porosity. Specific examples of such substrates include unglazed concrete, brick, tile, stone including granite, limestone and marble, grout, mortar, statuary, monuments, wood, composite materials such as terrazzo, and wall and ceiling panels including those fabricated with gypsum board. These are used in the construction of buildings, roads, parking ramps, driveways, floorings, fireplaces, fireplace hearths, counter tops, and other decorative uses in interior and exterior applications.

The compositions of the present invention are useful to provide one or more of excellent water repellency, oil repellency, and stain resistance to treated substrates. They also are useful to provide resistance to blocking, open time extension, and oil repellency to substrates coated with a coating composition to which the compositions of the present invention have been added. These properties are obtained using lower fluorine concentrations compared with conventional perfluorocarbon surface treatment agents, providing improved "fluorine efficiency" in the protection of treated surfaces The compositions of the present invention are effective at fluorine concentrations about one half to one third of the fluorine concentration for conventional fluorochemical surface protectants. The compositions of the present invention also allow for the use of shorter fluoroalkyl groups containing 6 or fewer fluorinated carbon atoms while conventional commercially available surface treatment products typically show poor oil repellency and water repellency performance if the fluoroalkyl groups contain less 8 carbon atoms.

Materials and Test Methods

The following materials and test methods were used in the examples herein.

$C_6F_{13}CH_2CH_2OH$ and $C_4F_9CH_2CH_2OH$ are commercially available from Sigma Aldrich, St. Louis, Mo.

$i-C_3F_7CF_2CF_2CH_2CH_2OH$ is commercially available from SynQuest Labs, Inc.

$C_4F_9CH_2CF_2CH_2CH_2OH$ was produced by introducing ethylene (25 g, 0.53 mol) was introduced to an autoclave charged with $C_4F_9CH_2CF_2I$ (217 g, 0.87 mol) and d-(+)-limonene (1 g), and then the reactor was heated at 240° C. for 12 hours. Product was obtained via vacuum distillation 81~91° C. at 19~24 mmHg in 62% yield. Fuming sulfuric acid (70 mL) was added slowly to 50 g of $C_4F_9CH_2CF_2CH_2CH_2I$ and mixture was stirred at 60° C. for 1.5 h. The reaction was quenched with ice-cold 1.5 wt % $Na_2SO_3$ aqueous solution and heated at 95° C. for 0.5 h. The bottom layer was separated and washed with 10 wt % aqueous sodium acetate and distilled to provide compound of formula $C_4F_9CH_2CF_2CH_2CH_2OH$: by 54-57° C. at 2 mmHg (267 Pascals).

$C_3F_7OCF_2CF_2CH_2CH_2OH$ was produced by charging $C_3F_7OCF_2CF_2I$ (100 g, 0.24 mol) and benzoyl peroxide (3 g) to a pressure vessel under nitrogen. A series of three vacuum/nitrogen gas sequences was then executed at −50° C. and ethylene (18 g, 0.64 mol) was introduced. The vessel was heated for 24 hour at 110° C. The autoclave was cooled to 0° C. and opened after degassing. Then the product was collected in a bottle. The product was distilled giving 80 g of $C_3F_7OCF_2CF_2CH_2CH_2I$ in 80% yield. The boiling point was 56-60° C. at 25 mm Hg (3333 Pa). A mixture of $C_3F_7OCF_2CF_2CH_2CH_2I$ (300 g, 0.68 mol) and N-methylformamide (300 mL), was heated to 150° C. for 26 h. Then the reaction was cooled to 100° C., followed by the addition of water to separate the crude ester. Ethyl alcohol (77 mL) and p-toluene sulfonic acid (2.59 g) were added to the crude ester, and the reaction was stirred at 70° C. for 15 minutes. Then ethyl formate and ethyl alcohol were distilled out to give a crude product. The crude product was dissolved in ether, washed with aqueous sodium sulfite, water, and brine in turn, and then dried over magnesium sulfate. The product was then distilled to give 199 g of $C_3F_7OCF_2CF_2CH_2CH_2OH$ in 85% yield. The boiling point was 71-73° C. at 40 mm Hg (5333 Pa).

L-lysine and L-Arginine are commercially available from Sigma Aldrich, St. Louis, Mo.

RHOPLEX 3829, formulation N-29-1, is commercially available from The Dow Chemical Company, Philadelphia, Pa.

MAB paints have an acrylic semi-gloss resin with 84% gloss at 85 degrees and are commercially available from M. A. Bruder and Sons, Inc., Broomall, Pa.

Methods

Test Method 1—Surface Tension Measurement

Surface tension was measured according to the American Society for Testing and Materials ASTM #D1331-56, using the Wilhelmy plate method on a KRUSS K11 Version 2.501 tensiometer (KRUSS USA, 5 Matthews N.C.) in accordance with instructions with the equipment. A vertical plate of known perimeter was attached to a balance, and the force due to wetting was measured. Each example to be tested was added to a coating composition by weight based on solids of the additive in deionized water. Several different concentrations were prepared. Ten replicates were tested of each dilution, and the following machine settings were used: Method: Plate Method SFT, interval: 1.0 s, wetted length: 40.2 mm, reading limit: 10, min standard deviation: 2 dynes/cm, and Gr. Acc.: 9.80665 m/s2.

Results were in dynes/cm (mN/m) with a Standard Deviation of less than 1 dyne/cm. The tensiometer was used according to the manufacturer's recommendations. A stock solution was prepared for the highest concentration of surfactant in the coating composition to be analyzed. The concentration of the solution was by mol percent of the surfactant in a commercially available floor polish (RHOPLEX 3829, Formulation N-29-1), in deionized water, and in 2% KCl solution in water. The solutions are stirred overnight (for approximately 12 hours) to ensure complete mixing. Lower concentrations of the stock solution for each example were made by diluting the original stock solution. The floor polish is used for applications in the consumer, institutional, and industrial cleaning segments for demonstration of providing surface effects to substrates. Lower surface tension results indicate superior performance.

Test Method 2-Blocking Resistance of Architectural Latex Paints

The test method described herein is a modification of ASTM D4946-89—Standard Test Method for Blocking Resistance of Architectural Paints.

The face-to-face blocking resistance of paints to be tested was evaluated in this test. Blocking, for the purpose of this test, is defined as the undesirable sticking together of two painted surfaces when pressed together or placed in contact with each other for an extended period of time.

The paint to be tested was cast on a polyester test panel using an applicator blade. All painted panels were protected from grease, oil, fingerprints, dust, et cetera, to avoid surface contamination that could affect blocking resistance results. Typically, results are evaluated at 24 hours after casting the paint. After the panels have been conditioned in the conditioned room as specified in the ASTM Method referenced above for the desired period of time, six squares (3.8 cm×3.8 cm) were cut out from the painted test panel. The cut sections (three pairs) were placed with the paint surfaces face-to-face for each of the paints to be tested. The cut sections (three pairs) are placed with the paint surfaces face-to-face for each of the paints to be tested. The face-to-face specimens were placed in a 50° C. oven on a marble tray. A no. 8 stopper was placed on top, with the smaller diameter in contact with the specimens, and then a 1000 g weight was placed on top of the stopper. This resulted in a pressure of 1.8 psi ($12.4 \times 10^3$ Pa) on the specimens. One weight and stopper was used for each specimen tested. After exactly 30 minutes, the stoppers and weights were taken off the test specimens which were removed from the oven and allowed to cool in the conditioned room for 30 minutes before determining resistance to blocking.

After cooling, the specimens were separated by peeling apart with a slow and steady force. The blocking resistance was rated from 0 to 10, corresponding to a subjective tack assessment (sound made upon separation of the painted specimens) or seal (complete adhesion of the two painted surfaces) as determined by the operator of the method. The specimen was put near the ear to actually hear the degree of tack. The rating system is described in Table 1. The degree of seal was estimated from the appearance of the specimens and the fraction of the paint surfaces that adhere. Paint tearing away from the test panel backing was an indication of seal. A higher number indicates better resistance to blocking.

TABLE 1

Blocking Resistance Numerical Ratings

| Blocking Resistance Numerical Ratings | Description of the Separation | Performance Description |
| --- | --- | --- |
| 10 | No tack | Perfect |
| 9 | Trace tack | Excellent |
| 8 | Very slight tack | Very good |
| 7 | Slight tack | Good/very good |
| 6 | Moderate to slight tack | Good |
| 5 | Moderate tack | Fair |
| 4 | Very tacky - no seal | Poor to fair |
| 3 | 5 to 25% seal | Poor |
| 2 | 25 to 50% seal | Poor |
| 1 | 50 to 75% seal | Very poor |
| 0 | 75 to 100% seal | Very poor |

Test Method 3—Contact Angle

Contact angles were measured by the Sessile Drop Method, which is described by A. W. Adamson in The Physical Chemistry of Surfaces, Fifth Edition, Wiley & Sons, New York, N.Y., 1990. Additional information on the equipment and procedure for measuring contact angles is provided by R. H. Dettre et al. in "Wettability", Ed. by J. C. Berg, Marcel Dekker, New York, N.Y., 1993. In the Sessile Drop Method, a Rame-Hart optical bench (available from Rame-Hart Inc., 43 Bloomfield Ave., Mountain Lakes, N.J.) was used to hold the substrate in the horizontal position. The contact angle was measured at a prescribed temperature with a telescoping goniometer from the same manufacturer. Each Example to be tested was added to MAB paint at 0.018% by weight based on solids of the additive in the paint. A drop of test liquid was placed on a polyester scrub test panel (Leneta P-121 dull black or equivalent, Leneta Company, Mahwah, N.J.) and the tangent was precisely determined at the point of contact between the drop and the surface. An advancing angle was determined by increasing the size of the drop of liquid. The data were presented as advancing contact angles.

The relationship between organic liquid contact angles, and the cleanability and dirt retention of surfaces is described by A. W. Adamson, above. In general, higher hexadecane contact angles indicate that a surface has greater dirt and soil repellency, and easier surface cleanability.

Test Method 4—Wetting/Leveling Test

To test the performance of the samples in their wetting and leveling ability, the samples were added to a floor polish (RHOPLEX 3829, Formulation N-29-1, available from The Dow Chemical Company, Philadelphia, Pa.]) and applied to half of a thoroughly cleaned 12 inch×12 inch (30.36 cm×30.36 cm) vinyl tile (available from Interfuse Vinyl Tiles by Estrie, Sherbrooke, QC Canada). The tiles are thoroughly cleaned by wetting the tiles, adding a powdered oxygen bleach cleanser and scrubbing using a green SCOTCH-BRITE scouring pad, available from 3M Company, St. Paul Minn.). This scrubbing procedure was used to remove the pre-existing coating on the tiles. The tiles initially have a uniform shiny finish; a uniform dull finish indicates coating removal. The tiles are then air-dried overnight. A 1 wt % solution of the surfactant to be tested was prepared by dilution in deionized water. Following the resin manufacturer protocols, a 100 g portion of the RHOPLEX 3829, N-29-1 formulation was prepared, followed by addition of 0.75 g of the 1 wt % surfactant solution, to provide a test floor polish.

The test floor polish was applied to the tile by placing 3 mL portion of the test polish in the center of the tile, and spreading from top to bottom using a cheesecloth applicator, and finally placing a large "X" across the tile, using the applicator. The "X" subsequently provides visual evidence of leveling at the rating step. The applicator was prepared from a two-layer 18×36 inch (46×91 cm) sheet of cheesecloth (from VWR, West Chester Pa.), folded twice into an eight-layer pad. One corner of the pad was then used as the applicator. The tile was allowed to dry for 30 min. and a total of 5 coats (Coating #s 1-5) were applied and dried, with the X test performed after each coating had been dried. After each coat, the tile was rated on a 1 to 5 scale (1 being the worst, 5 the best) on the surfactant's ability to promote wetting and leveling of the polish on the tile surface. The rating is determined using the Tile Rating Scale below, based on comparison of a tile treated with the floor polish that contains no added surfactant.

TABLE 2

Visual Tile Rating Scale for Leveling

| Score | Description |
|---|---|
| 1 | Uneven surface coverage of the film, significant streaking and surface defects |
| 2 | Numerous surface defects and streaks are evident but, generally, film coats entire tile surface |
| 3 | Visible streaking and surface defects, withdrawal of the film from the edges of the tile |
| 4 | Minor surface imperfections or streaking |
| 5 | No visible surface defects or streaks |

Test Method 5—Blender Foaming Test

The test procedure used to evaluate the foaming of fluorosurfactants for oilfield (e.g. drilling and stimulation) and cleaning applications is a modified version of the blender foaming test ASTM D3519-88—Standard Test Method for Foam in Aqueous Media (Blender Test). The ability of the samples to create foam and maintain stable foam in aqueous solution over a period of time was evaluated in this test. A blender, graduated cylinder, glass sample bottles and a stop watch were the only materials required. First, stock solutions of the testing base solutions were made. These solutions were deionized water and 2% KCl Samples of 100 mL of the fluorosurfactant to be tested at 0.1% active ingredient in the desired base testing solution were prepared and stirred overnight to ensure complete mixing. The blender was cleaned with copious amounts of deionized water. Once clean, the blender was assembled for use. The test fluid sample of 100 mL was poured into the blender jar. The temperature of the test fluid was measured with a thermometer and recorded. The blender was then run for 20 seconds at 50-60% power. After 20 seconds, the liquid and foam were immediately poured into a 500 mL graduated cylinder. The initial liquid and foam height were measured in mL and a timer was started. This was designated the maximum total foam height at time zero. The graduated cylinder was allowed to stand undisturbed. Additional liquid and foam height (in mL) measurements were taken 5, 10 and 15 minutes after the stop watch was started. In addition, the half-life of the foam was also recorded. The half-life was the time when half of the liquid had drained to the bottom of the graduated cylinder. During this time, any observations of the foam were recorded such as dense or thin foam and foam persistency. A larger height (in mL) of the foam indicated that the sample foamed more. A consistently high height (in mL) of foam demonstrated persistent foam. The blender foaming test was used as an indicator of the amount of foam that a sample produced and also displayed the persistence of that foam.

EXAMPLES

Example 1

Phosphorous pentoxide (5.24 g, 0.03692 mol) was added to $C_6F_{13}CH_2CH_2OH$ (30 g, 0.08242 mol) at 80° C. and the reaction was heated to 105° C. overnight. The reaction mixture was cooled to 60° C. and added to aqueous lysine solution (12.77 g lysine in 181 mL water). The mixture was stirred for 1 hour at 70° C. The resulting product was tested from surface tension, contact angle, resistance to blocking, and leveling as described below with results in Tables 3 to 7.

Example 2

Phosphorous pentoxide (1.23 g, 0.008682 mol) was added to $C_4F_9CH_2CH_2OH$ (5.12 g, 0.01938 mol) at 80° C. and the reaction was heated to 105° C. overnight. The reaction mixture was cooled to 60° C., followed by adding aqueous lysine solution (3 g lysine in 37 g water) addition. This phosphate lysine salt solution was stirred for 1 hour at 70° C. The resulting product was tested from surface tension, contact angle, resistance to blocking, and leveling as described below with results in Tables 3 to 7.

Example 3

Phosphorous pentoxide (0.97 g, 0.00683 mol) was added to $C_4F_9CH_2CF_2CH_2CH_2OH$ (5 g, 0.01524 mol) at 80° C. and the reaction was heated to 105° C. overnight. The reaction mixture was cooled to 60° C., followed by adding aqueous lysine solution (2.36 g lysine in 33 g water). This phosphate lysine salt solution was stirred for 1 hour at 70° C. The resulting product was tested from surface tension, contact angle, resistance to blocking, and leveling as described below with results in Tables 3 to 7.

Example 4

Phosphorous pentoxide (0.96 g, 0.00679 mol) was added to $C_3F_7OCF_2CF_2CH_2CH_2OH$ (5 g, 0.01515 mol) at 80° C. and the reaction was heated to 105° C. overnight. The reaction mixture was cooled to 60° C., followed by adding aqueous lysine solution (2.34 g lysine in 47 g water). This phosphate lysine salt solution was stirred for 1 hour at 70° C. The resulting product was tested from surface tension, contact angle, resistance to blocking, and leveling as described below with results in Tables 3 to 7.

Example 5

Phosphorous pentoxide (1.01 g, 0.00713 mol) was added to i-$C_3F_7CF_2CF_2CH_2CH_2OH$ (5 g, 0.01592 mol) at 80° C. and the reaction was heated to 105° C. overnight. The reaction mixture was cooled to 60° C., followed by adding aqueous lysine solution (2.94 g lysine in 34 g water). This phosphate lysine salt solution was stirred for 1 hour at 70° C.

The resulting product was tested from surface tension, contact angle, resistance to blocking, and leveling as described below with results in Tables 3 to 7.

Example 6

Phosphorous pentoxide (0.87 g, 0.006154 mol) was added to $C_6F_{13}CH_2CH_2OH$ (5 g, 0.01374 mol) at 80° C. and the reaction was heated to 105° C. overnight. The reaction mixture was cooled to 60° C., followed by adding aqueous arginine solution (2.54 g arginine in 34 g water) addition. This phosphate lysine salt solution was stirred for 1 hour at 70° C. The resulting product was tested from surface tension, contact angle, resistance to blocking, and leveling as described below with results in Tables 3 to 7.

Example 7

Phosphorous pentoxide (1.20 g, 0.008485 mol) was added to $C_4F_9CH_2CH_2OH$ (5 g, 0.01894 mol) at 80° C. and the reaction was heated to 105° C. overnight. The reaction mixture was cooled to 60° C., followed by adding aqueous arginine solution (3.5 g arginine in 39 g water) addition. This phosphate lysine salt solution was stirred for 1 hour at 70° C. The resulting product was tested from surface tension, contact angle, resistance to blocking, and leveling as described below with results in Tables 3 to 7.

Example 8

Phosphorous pentoxide (0.97 g, 0.00683 mol) was added to $C_4F_9CH_2CF_2CH_2CH_2OH$ (5 g, 0.01524 mol) at 80° C. and the reaction was heated to 105° C. overnight. The reaction mixture was cooled to 60° C., followed by adding aqueous arginine solution (2.81 g arginine in 35 g water) addition. This phosphate lysine salt solution was stirred for 1 hour at 70° C. The resulting product was tested from surface tension, contact angle, resistance to blocking, and leveling as described below with results in Tables 3 to 7.

Example 9

Phosphorous pentoxide (0.96 g, 0.00679 mol) was added to $C_3F_7OCF_2CF_2CH_2CH_2OH$ (5 g, 0.01515 mol) at 80° C. and the reaction was heated to 105° C. overnight. The reaction mixture was cooled to 60° C., followed by adding aqueous arginine solution (2.8 g arginine in 35 g water) addition. This phosphate lysine salt solution was stirred for 1 hour at 70° C. The resulting product was tested from surface tension, contact angle, resistance to blocking, and leveling as described below with results in Tables 3 to 7.

Example 10

Phosphorous pentoxide (1.01 g, 0.00713 mol) was added to i-$C_3F_7CF_2CF_2CH_2CH_2OH$ (5 g, 0.01592 mol) at 80° C. and the reaction was heated to 105° C. overnight. The reaction mixture was cooled to 60° C., followed by adding aqueous arginine solution (2.94 g arginine in 36 g water) addition. This phosphate lysine salt solution was stirred for 1 hour at 70° C. The resulting product was tested from surface tension, contact angle, resistance to blocking, and leveling as described below with results in Tables 3 to 7.

Comparative Example A

Phosphorus pentoxide (1 equivalent) was added to a perfluoroalkylethyl alcohol mixture of the formula $F(CF_2)_zCH_2CH_2OH$ (2.3 equivalents). at 80° C. The typical mixture was as follows: 1.6% of z=4, 48.3% of z=6, 28.7% of z=8, 13.9% of z=10, 5.3% of z=12, 1.7 of z=14, 0.4% of z=16 and 0.1% of z=18. The reaction was heated to 105° C. for 24 hours. Ammonia (30% solution in water, 2.6 equivalents) was added and the reaction was stirred for 10 min. at 70° C. Water was added and the reaction was stirred at 70° C. for 1 hour to provide a phosphate product. The resulting product was tested for leveling, surface tension, contact angle, and resistance to blocking using Test Methods 1 to 4. The results are listed in Tables 3 to 7.

TABLE 3

Surface Tension in DI Water (dynes/cm) at 23 deg C.

| Example* | 0.000% | 0.001% | 0.010% | 0.100% | 0.500% |
|---|---|---|---|---|---|
| 1 | 72.2 | 64.1 | 25.7 | 23.8 | 26.9 |
| 2 | 72.1 | 58.4 | 44.7 | 27.4 | 16.4 |
| 3 | 72.3 | 46.9 | 33.4 | 18.2 | 16.5 |
| 4 | 72.3 | 38.7 | 26.6 | 18.2 | 17.1 |
| 5 | 72.0 | 47.4 | 36.5 | 21.6 | 19.0 |
| 6 | 72.4 | 66.4 | 24.6 | 21.6 | 22.0 |
| 7 | 72.6 | 57.0 | 42.0 | 25.1 | 17.0 |
| 8 | 72.6 | 46.9 | 32.2 | 16.8 | 17.0 |
| 9 | 72.2 | 40.7 | 26.0 | 20.1 | 18.0 |
| 10 | 72.3 | 40.2 | 33.0 | 19.4 | 17.7 |
| Comparative Example | 72.2 | 61.8 | 39.2 | 34.3 | 26.3 |

*Example was added to deionized water by weight based on solids of the additive in DI water.
*Standard Deviation <1 dynes/cm Normal surface tension of deionized water is 72 dynes/cm (shown in Table 3 as 0.000%). When the compounds of the present invention were added at a specified rate, the surface tension of each aqueous solution was reduced significantly. Better performance was obtained at higher levels.

TABLE 4

Surface Tension in Rhoplex 3829 (N-29-1 Formulation) Floor Finish (dynes/cm) at 23° C.

| Example* | 0.000% | 0.001% | 0.010% | 0.100% | 0.500% |
|---|---|---|---|---|---|
| 1 | 32.2 | 31.5 | 27.8 | 17.3 | 16.1 |
| 2 | 32.3 | 31.6 | 30.1 | 24.4 | 19.5 |
| 3 | 32.3 | 31.2 | 30.3 | 25.3 | 19.9 |
| 4 | 32.1 | 31.8 | 27.4 | 19.1 | 16.8 |
| 5 | 32.2 | 29.2 | 29.0 | 22.7 | 18.1 |
| 6 | 32.3 | 31.7 | 27.8 | 17.9 | 16.4 |
| 7 | 32.2 | 32.1 | 30.6 | 24.8 | 19.5 |
| 8 | 32.0 | 31.8 | 29.7 | 25.8 | 20.1 |
| 9 | 32.4 | 31.9 | 28.2 | 19.9 | 16.5 |
| 10 | 32.5 | 31.9 | 29.7 | 23.6 | 17.9 |
| Comparative Example | 32.5 | 31.3 | 28.2 | 21.0 | 20.3 |

*Concentration of examples in floor finish, % by weight.
*Standard Deviation <1 dynes/cm Normal surface tension of the RHOPLEX 3829, formulation N-29-1 coating composition is 32 dynes/cm. When the above examples of the present invention were added at a specified rate, the surface tension of each aqueous coating composition solution was significantly reduced. Better performance (lower surface tension values) was obtained at higher levels, which is indicative of improved wetting and leveling properties. Examples 1-10 performed equal or better with surface tension reduction than the Comparative Example comprising fluorinated phosphate having longer perfluorinated alkyl groups and a higher fluorine loading.

TABLE 5

Resistance to Blocking in Semi-Gloss Latex Paint

| Example* | Blocking Rating** | Fluorine (ppm) |
|---|---|---|
| Control | 2.7 | 0 |
| 1 | 8.7 | 85 |
| 2 | 7.3 | 71 |
| 3 | 8.3 | 76 |
| 4 | 8.0 | 76 |
| 5 | 8.0 | 78 |
| 6 | 8.3 | 81 |
| 7 | 7.3 | 67 |
| 8 | 7.0 | 73 |
| 9 | 7.3 | 72 |
| 10 | 7.3 | 74 |
| Comparative Example | 8.2 | 114 |

*Example was added to paint at 0.02% based on solids by weight based on solids of the additive in the paint
**Average of 3 replicates The data in Table 5 demonstrates that excellent resistance to blocking was obtained from the present invention compared to the Comparative Example at much lower fluorine content.

TABLE 6

Advancing Contact Angle in Semi-Gloss Latex Paint

| Example* | Hexadecane | F (ppm) |
|---|---|---|
| Control | 0 | 0 |
| 1 | 81.3 | 85 |
| 2 | 84.5 | 71 |
| 3 | 82.2 | 76 |
| 4 | 98.8 | 76 |
| 5 | 95.8 | 78 |
| 6 | 81.9 | 81 |
| 7 | 87.5 | 67 |
| 8 | 73.6 | 73 |
| 9 | 92.5 | 72 |
| 10 | 83.6 | 74 |
| Comparative Example | 81.4 | 114 |

*Example added to paint at 0.02 wt % based on solids of the additive in the paint The data in Table 6 show excellent increased hexadecane contact angle for all examples of the present invention compared to the control.

The increase in the advancing hexadecane contact angle correlates with improved oil repellency. The present invention also performs equal to or better than the comparative example at significant lower F loading.

The product was added to floor polish in an amount of 0.75 wt % of 1 wt % the surfactant dilution and tested for leveling using Test Method 3. Results are shown in Table 7.

TABLE 7

Leveling in RHOPLEX 3829 (N-29-1 Formulation) Floor Finish

| Examples | Reading* | F (ppm) |
|---|---|---|
| Blank | 1.2 | 0 |
| 1 | 3.3 | 32 |
| 2 | 3.3 | 27 |
| 3 | 3.3 | 29 |
| 4 | 3.1 | 29 |
| 5 | 3.1 | 30 |
| 6 | 3.3 | 30 |
| 7 | 3.2 | 25 |
| 8 | 3.1 | 27 |
| 9 | 3.3 | 27 |
| 10 | 3.1 | 28 |
| Comparative Example | 3.6 | 43 |

*Average of 5 coats

The phosphates exhibited excellent wetting ability in a commercially available floor finish (RHOPLEX 3829 N-29-1 formulation). They performed equally to the Comparative Example comprising fluorinated phosphate having longer perfluorinated alkyl groups and a much higher fluorine loading when tested on vinyl tile.

TABLE 8

Surface Tension in 2% KCl (dynes/cm) at 23 deg C.

| Example* | 0.000% | 0.001% | 0.010% | 0.100% | 0.500% |
|---|---|---|---|---|---|
| 1 | 73.5 | — | — | — | — |
| 2 | 73.3 | 46.0 | 24.0 | 15.8 | 16.0 |
| 3 | 73.5 | 48.6 | 19.9 | 17.3 | 17.3 |
| 4 | 72.9 | 28.3 | 19.4 | 18.8 | 15.1 |
| 5 | 73.4 | 29.8 | 17.9 | 17.6 | 16.9 |
| 6 | 73.5 | — | — | — | — |
| 7 | 73.5 | 43.2 | 23.0 | 16.1 | 14.5 |
| 8 | 74.2 | 38.5 | 19.0 | 18.2 | 16.1 |
| 9 | 73.5 | 46.8 | 20.3 | 19.5 | 17.3 |
| 10 | 73.4 | 34.2 | 18.5 | 17.1 | 17.5 |
| Comparative Example | 73.6 | 68.4 | 50.2 | 32.9 | 29.0 |

— = not tested

Normal surface tension of 2% KCl water is 73.5 dynes/cm (shown in Table X as 0.000%). Example 1 and 6 were not stable in 2% KCl. When the above phosphate was added at a specified rate, the surface tension of each aqueous solution was reduced significantly. Better performance was obtained at higher levels. According to the results from the test, excellent surface tension reduction was seen from the present invention that outperforms the Comparative Example. Improved surface tension reduction in brine is desirable for oilfield stimulation and drilling fluid applications.

TABLE 9

Blender Foaming in Deionized Water

| | Foam Volume (mL) | | | |
|---|---|---|---|---|
| Example | Initial | t = 5 min | t = 10 min | t = 15 min |
| 1 | 110 | 5 | 5 | 5 |
| 2 | 245 | 115 | 100 | 85 |
| 3 | 220 | 123 | 11 | 110 |
| 4 | 210 | 120 | 100 | 90 |
| 5 | 200 | 100 | 82 | 75 |
| 6 | 8 | 7 | 7 | 2 |
| 7 | 245 | 140 | 110 | 95 |
| 8 | 210 | 110 | 90 | 81 |

TABLE 9-continued

Blender Foaming in Deionized Water

| | Foam Volume (mL) | | | |
|---|---|---|---|---|
| Example | Initial | t = 5 min | t = 10 min | t = 15 min |
| 9 | 200 | 100 | 83 | 80 |
| 10 | 185 | 86 | 75 | 71 |
| Comparative Example | 0 | 0 | 0 | 0 |

TABLE 10

Blender Foaming in 2% KCl

| | Foam Volume (mL) | | | |
|---|---|---|---|---|
| Example | Initial | t = 5 min | t = 10 min | t = 15 min |
| 1 | — | — | — | — |
| 2 | 170 | 31 | 30 | 30 |
| 3 | 150 | 39 | 34 | 34 |
| 4 | 130 | 25 | 21 | 18 |
| 5 | 25 | 15 | 15 | 15 |
| 6 | — | — | — | — |
| 7 | 175 | 29 | 28 | 28 |
| 8 | 135 | 30 | 30 | 30 |
| 9 | 125 | 26 | 24 | 19 |
| 10 | 115 | 14 | 122 | 10 |
| Comparative Example | 14 | 7 | 0 | 0 |

Examples 1 and 6 were not stable in 2% KCl and thus the blender foaming test could not be conducted.
— = not tested The blender foaming results in deionized water and 2% KCl shown in Tables 9 and 10, respectively, demonstrated improved foaming and more sustainable foam with time over the Comparative Example. Foaming properties are desirable for cleaning solutions where the foam is used to promote adhesion of the active cleaning ingredient on the surface. In oilfield stimulation and drilling applications surfactant additives that help boost the foaming properties of the fluids are desirable.

What is claimed is:

1. A composition comprising formula I, formula II, or formula

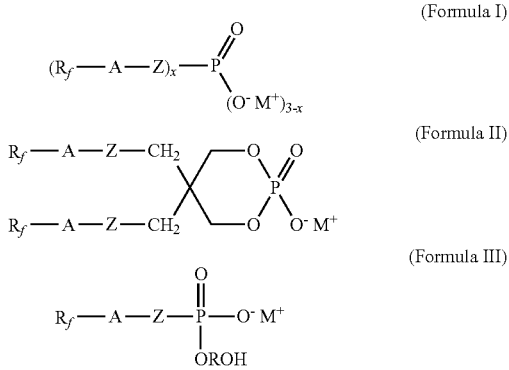

(Formula I)

(Formula II)

(Formula III)

wherein
$R_f$ is a $C_1$ to $C_6$ linear or branched perfluoroalkyl optionally interrupted by one, two or three ether oxygen atoms;
x is 1 to 2;
A is $(CH_2)_k$, $(CH_2CF_2)_m(CH_2)_n$, $(CH_2)OSO_2N(CH_3)(CH_2)_p$, $O(CF_2)_2(CH_2)_r$, or $OCHFCF_2OE$;
Z is O or S;
m is 1 to 4;
k, n, o, p, and r are each independently 1 to 20;
E is a $C_2$ to $C20$ linear or branched alkyl group optionally interrupted by oxygen, sulfur, or nitrogen atoms; a cyclic alkyl group, or a $C_6$ to $C_{10}$ aryl group;
R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2; and
M is an ammonium cation $(NH_2R^1R^2)^+$ wherein $R^1$ and $R^2$ are linear or branched organic groups which, collectively as $R^1R^2$, contain at least one carboxylate moiety and one amino moiety, said linear or branched organic groups being optionally substituted, interrupted, or both with sulfur-containing moieties, nitrogen-containing moieties, cyclic alkyl moieties, or aryl moieties, where said cyclic alkyl or aryl moieties contain up to 10 carbon atoms.

2. A composition of claim 1, wherein $R_f$ is a $C_4$ to $C_6$ linear perfluoroalkyl, A is $(CH_2)_k$, and k is 2.

3. A composition of claim 1, wherein $R_f$ is a $C_4$ to $C_6$ linear perfluoroalkyl, A is $(CH_2CF_2)_m(CH_2)_n$, m is 1, and n is 2.

4. A composition of claim 1, wherein $R_f$ is a $C_3$ linear perfluoroalkyl A is $O(CF_2)_2(CH_2)_r$, and r is 2.

5. A composition of claim 1, wherein M is an ammonium cation $(NH_2R^1R^2)^+$ wherein $R^1$ and $R^2$ are unsubstituted and uninterrupted linear or branched organic groups which, collectively as $R^1R^2$, contain at least one carboxylate moiety and one amino moiety.

6. A composition comprising formula I, formula II, or formula III

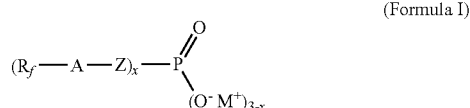

(Formula I)

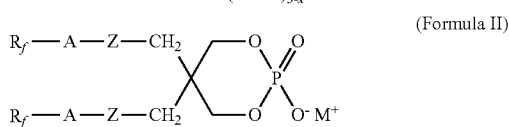

(Formula II)

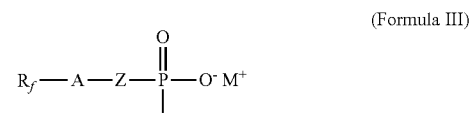

(Formula III)

wherein
$R_f$ is a $C_1$ to $C_6$ linear or branched perfluoroalkyl optionally interrupted by one, two or three ether oxygen atoms;
x is 1 to 2;
A is $(CH_2)_k$, $(CH_2CF_2)_m(CH_2)_n$, $(CH_2)OSO_2N(CH_3)(CH_2)_p$, $O(CF_2)_2(CH_2)_r$, or $OCHFCF_2OE$;
Z is O or S;
m is 1 to 4;
k, n, o, p, and r are each independently 1 to 20;
E is a $C_2$ to $C_{20}$ linear or branched alkyl group optionally interrupted by oxygen, sulfur, or nitrogen atoms; a cyclic alkyl group, or a $C_6$ to $C_{10}$ aryl group;

R is a $C_2$ to $C_{10}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2; and wherein M is

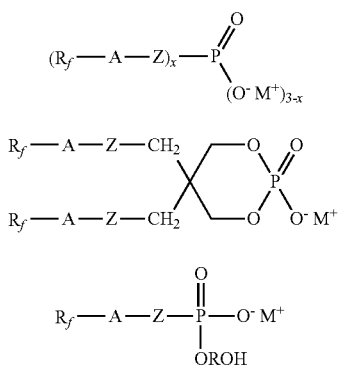

7. A composition comprising formula I, formula II, or formula III

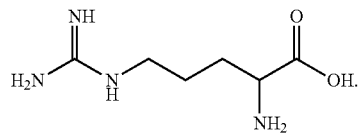 [SMILES: N=C(N)NCCCC(N)C(=O)O]
(Formula I)

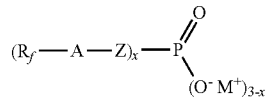 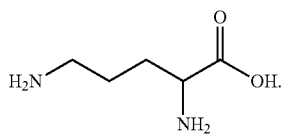

(Formula II)

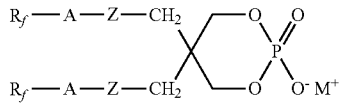

(Formula III)

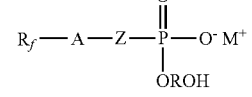

wherein
R$_f$ is a $C_1$ to $C_6$ linear or branched perfluoroalkyl optionally interrupted by one, two or three ether oxygen atoms;
x is 1 to 2;
A is $(CH_2)_k$, $(CH_2CF_2)_m(CH_2)_n$, $(CH_2)OSO_2N(CH_3)(CH_2)_p$, $O(CF_2)_2(CH_2)_r$, or $OCHFCF_2OE$;
Z is O or S;
m is 1 to 4;
k, n, o, p, and r are each independently 1 to 20;
E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
R is a $C_2$ to $C_{10}$ linear or branched alkyl group optionally interrupted by hetero atoms selected from the group consisting of an oxygen, sulfur, or nitrogen atom: a cyclic alkyl; or a $C_6$ to $C_{10}$ aryl; provided that when R is greater than 8 carbons, the ratio of hetero atoms to carbon atoms is at least 1:2; and
where M is an ammonium cation $(NH_3R)^4$ wherein R is linear or branched organic group containing at least one carboxylate moiety and one amino moiety, said linear or branched organic groups being optionally substituted, interrupted, or both with sulfur-containing moieties, nitrogen-containing moieties, cyclic alkyl moieties, or aryl moieties, where said cyclic alkyl or aryl moieties contain up to 10 carbon atoms.

8. A composition of claim 7, wherein M is

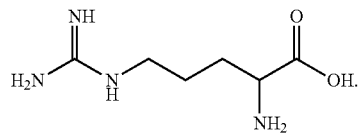 [SMILES: N=C(N)NCCCC(N)C(=O)O]

9. A method of lowering the surface tension of a liquid comprising contacting a liquid to a composition comprising formula I, formula II, or formula III

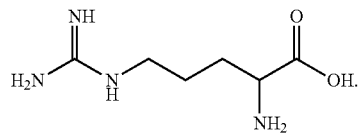 [SMILES: N=C(N)NCCCC(N)C(=O)O]
(Formula I)

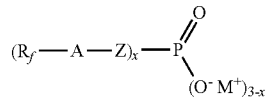 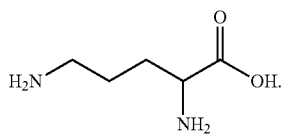

(Formula II)

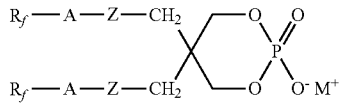

(Formula III)

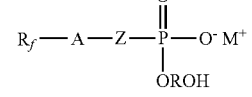

wherein
R$_f$ is a $C_1$ to $C_6$ linear or branched perfluoroalkyl optionally interrupted by one, two or three ether oxygen atoms;
x is 1 to 2;
A is $(CH_2)_k$, $(CH_2CF_2)_m(CH_2)_n$, $(CH_2)OSO_2N(CH_3)(CH_2)_p$, $O(CF_2)_2(CH_2)_r$, or $OCHFCF_2OE$;
Z is O or S;
m is 1 to 4;
k, n, o, p, and r are each independently 1 to 20;
E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2; and
M is an ammonium cation $(NH_2R^1R^2)^+$ wherein $R^1$ and $R^2$ are linear or branched organic groups which, collectively as $R^1R^2$, contain at least one carboxylate moiety and one amino moiety, said linear or branched organic groups being optionally substituted, interrupted, or both with sulfur-containing moieties, nitrogen-containing moieties, cyclic alkyl moieties, or aryl moieties, where said cyclic alkyl or aryl moieties contain up to 10 carbon atoms.

10. The method of claim 9, wherein the liquid is selected from the group consisting of wherein the medium is water, saline solution, KCl solution, drill fluids, well fluids, liquid treatment or gas treatment stream for subterranean formation and well bore areas, hydrocarbon, halocarbon system, coating composition, latex, polymer, floor finish, floor polish, fire fighting agent, ink, emulsifying agent, foaming agent, release agent, repellency agent, flow modifier, film evaporation inhibitor, wetting agent, penetrating agent, cleaner, grinding agent, electroplating agent, corrosion inhibitor, etchant solution, soldering agent, dispersion aid, microbial agent, pulping aid, rinsing aid, polishing agent, personal care composition, drying agent, antistatic agent, or bonding agent.

11. The method of claim 10, wherein the coating composition is an alkyd coating, a Type I urethane coating, an unsaturated polyester coating, or a water-dispersed coating.

12. A composition comprising a liquid treated by contacting the liquid with a phosphate composition comprising formula I, formula II, or formula III

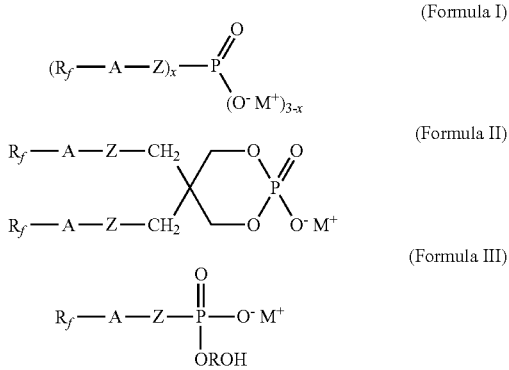

wherein
$R_f$ is a $C_1$ to $C_6$ linear or branched perfluoroalkyl optionally interrupted by one, two or three ether oxygen atoms;
x is 1 to 2;
A is $(CH_2)_k$, $(CH_2CF_2)_m(CH_2)_n$, $(CH_2)OSO_2N(CH_3)(CH_2)_p$, $O(CF_2)_2(CH_2)_r$, or $OCHFCF_2OE$;
Z is O or S;
m is 1 to 4;
k, n, o, p, and r are each independently 1 to 20;
E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2; and
M is an ammonium cation $(NH_2R^1R^2)^+$ wherein $R^1$ and $R^2$ are linear or branched organic groups which, collectively as $R^1R^2$, contain at least one carboxylate moiety and one amino moiety, said linear or branched organic groups being optionally substituted, interrupted, or both with sulfur-containing moieties, nitrogen-containing moieties, cyclic alkyl moieties, or aryl moieties, where said cyclic alkyl or aryl moieties contain up to 10 carbon atoms.

13. A method of imparting surface effects to a substrate comprising contacting at least a portion of a surface of the substrate with a coating composition containing a composition comprising formula I, formula II, or formula III

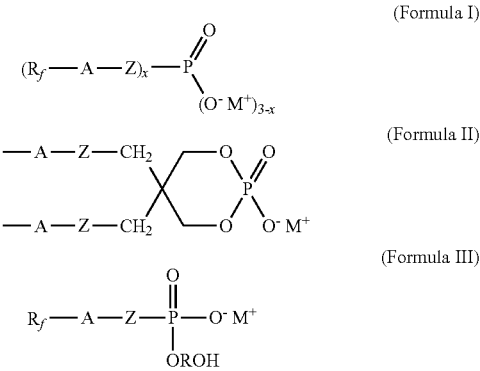

wherein
$R_f$ is a $C_1$ to $C_6$ linear or branched perfluoroalkyl optionally interrupted by one, two or three ether oxygen atoms;
x is 1 to 2;
A is $(CH_2)_k$, $(CH_2CF_2)_m(CH_2)_n$, $(CH_2)OSO_2N(CH_3)(CH_2)_p$, $O(CF_2)_2(CH_2)_r$, or $OCHFCF_2OE$;
Z is O or S;
m is 1 to 4;
k, n, o, p, and r are each independently 1 to 20;
E is a $C_2$ to $C_{20}$ linear or branched alkyl group optionally interrupted by oxygen, sulfur, or nitrogen atoms; a cyclic alkyl group, or a $C_6$ to $C_{10}$ aryl group;
R is a $C_2$ to $C_{60}$ linear or branched alkyl group optionally interrupted by hetero atoms selected from the group consisting of an oxygen, sulfur, or nitrogen atom; a cyclic alkyl; or a $C_6$ to $C_{10}$ aryl; provided that when R is greater than 8 carbons, the ratio of hetero atoms to carbon atoms is at least 1:2; and
M is an ammonium cation $(NH_2R^1R^2)^+$ wherein $R^1$ and $R^2$ are linear or branched organic groups which, collectively as $R^1R^2$, contain at least one carboxylate moiety and one amino moiety, said linear or branched organic groups being optionally substituted, interrupted, or both with sulfur-containing moieties, nitrogen-containing moieties, cyclic alkyl moieties, or aryl moieties, where said cyclic alkyl or aryl moieties contain up to 10 carbon atoms.

14. A method of claim 13, wherein the coating composition is an alkyd coating, a Type I urethane coating, an unsaturated polyester coating, or a water-dispersed coating.

15. A method of claim 13, wherein the surface effects are lowering surface tension, water repellency, oil repellency, stain resistance, soil resistance, and resistance to blocking, increased contact angle, wetting and leveling.

* * * * *